(12) United States Patent
Galinat et al.

(10) Patent No.: US 9,156,757 B2
(45) Date of Patent: Oct. 13, 2015

(54) PROCESS FOR THE OXIDATION OF HYDROCARBONS

(75) Inventors: Sophie Galinat, Lyons (FR); Françoise Igersheim, Lyons (FR); Serge Veracini, Lyons (FR)

(73) Assignee: RHODIA OPERATIONS, Paris (FR)

( * ) Notice: Subject to any disclaimer, the term of this patent is extended or adjusted under 35 U.S.C. 154(b) by 0 days.

(21) Appl. No.: 13/574,652

(22) PCT Filed: Jan. 14, 2011

(86) PCT No.: PCT/EP2011/050469
§ 371 (c)(1),
(2), (4) Date: Oct. 18, 2012

(87) PCT Pub. No.: WO2011/089074
PCT Pub. Date: Jul. 28, 2011

(65) Prior Publication Data
US 2013/0204038 A1    Aug. 8, 2013

(30) Foreign Application Priority Data
Jan. 21, 2010 (FR) ..................... 10 50386

(51) Int. Cl.
| | | |
|---|---|---|
| C07C 55/14 | (2006.01) |
| C07C 29/48 | (2006.01) |
| C07C 29/50 | (2006.01) |
| C07C 45/33 | (2006.01) |
| C07C 51/31 | (2006.01) |
| C07C 45/28 | (2006.01) |
| B01D 53/14 | (2006.01) |

(52) U.S. Cl.
CPC ............ *C07C 29/48* (2013.01); *B01D 53/1487* (2013.01); *B01D 53/1493* (2013.01); *C07C 29/50* (2013.01); *C07C 45/28* (2013.01); *C07C 45/33* (2013.01); *C07C 51/313* (2013.01); *B01D 53/1425* (2013.01); *B01D 2252/205* (2013.01); *B01D 2257/702* (2013.01); *C07C 2101/14* (2013.01)

(58) Field of Classification Search
CPC ........ C07C 51/215; C07C 7/06; C07C 29/48; C07C 45/28; C07C 29/50
See application file for complete search history.

(56) References Cited

U.S. PATENT DOCUMENTS

| | | | | |
|---|---|---|---|---|
| 3,131,228 A | * | 4/1964 | Moon | ............................. 95/191 |
| 3,340,304 A | * | 9/1967 | Schulz et al. | ................. 568/360 |
| 3,479,394 A | | 11/1969 | Brunie et al. | |
| 4,102,983 A | | 7/1978 | Yamase et al. | |
| 4,322,558 A | | 3/1982 | Risebury | |
| 4,877,903 A | | 10/1989 | Costantini et al. | |
| 4,923,485 A | * | 5/1990 | Horoldt et al. | ................. 95/208 |
| 5,505,920 A | | 4/1996 | Kollar et al. | |
| 5,772,734 A | | 6/1998 | Baker et al. | |
| 6,736,891 B1 | | 5/2004 | Bice et al. | |
| 2005/0288532 A1 | | 12/2005 | Genger et al. | |

FOREIGN PATENT DOCUMENTS

| | | |
|---|---|---|
| FR | 1230366 | 9/1960 |
| GB | 777087 | 6/1957 |
| GB | 857259 | 9/1960 |
| GB | 964896 | 7/1964 |
| GB | 1112837 | 5/1968 |
| GB | 1191573 | 5/1970 |
| JP | 5384941 | 7/1978 |
| JP | 01249735 | 10/1989 |
| JP | 2003-47823 A | 2/2003 |
| JP | 2003047823 | 2/2003 |
| JP | 2003507519 A | 2/2003 |
| JP | 2005536341 A | 12/2005 |
| RU | 2316385 C1 | 2/2008 |
| SU | 119867 | 9/1958 |
| WO | 0112730 A1 | 2/2001 |

OTHER PUBLICATIONS

Ewell et al, Industrial and Engineering Chemistry, Azeotropic Distillation, 36(10), pp. 871-875, 1944.*
International Search Report issued on Apr. 20, 2011 in International Patent Application No. PCT/EP2011/050469.

* cited by examiner

*Primary Examiner* — Paul A Zucker

(57) ABSTRACT

A method for oxidizing hydrocarbons, in particular saturated hydrocarbons, for producing peroxides, alcohols, ketones, aldehydes and/or diacids is described. Also described, is a method for oxidizing a cycloaliphatic saturated hydrocarbon using molecular oxygen for producing ketones/alcohols, and more precisely for oxidizing cyclohexane into cyclohexanol and cyclohexanone using molecular oxygen.

5 Claims, No Drawings

PROCESS FOR THE OXIDATION OF HYDROCARBONS

CROSS-REFERENCE TO PRIOR APPLICATIONS

This application is a National Stage of PCT/EP2011/050469, filed Jan. 14, 2011, and designating the United States (published in French on Jul. 28, 2011, as WO 2011/089074 A1; the title and abstract were published in English), which claims priority of FR 10 50386, filed Jan. 21, 2010, each hereby expressly incorporated by reference in its entirety and each assigned to the assignee hereof.

The present invention relates to a process for the oxidation of hydrocarbons, in particular of saturated hydrocarbons, for the production of peroxides, alcohols, ketones, aldehydes and/or diacids.

It relates more particularly to a process for the oxidation, via molecular oxygen, of a cycloaliphatic saturated hydrocarbon for the production of ketones/alcohols and more particularly still to the oxidation of cyclohexane via molecular oxygen to cyclohexanol and cyclohexanone.

The mixture of cyclohexanol and cyclohexanone or one of these products are used for the synthesis of adipic acid or of ε-caprolactam.

The process for manufacturing cyclohexanol and cyclohexanone by oxidation of cyclohexane via molecular oxygen or a gas containing molecular oxygen in the presence or absence of catalyst is described in many patents and many publications such as, for example, patents GB 777087, GB 1112837, GB 964896, GB 1191573, U.S. Pat. No. 3,479,394 and U.S. Pat. No. 4,877,903.

Generally, in such an oxidation process via molecular oxygen, the degree of conversion of the saturated hydrocarbon, such as cyclohexane, is deliberately kept at a low value in order to improve the selectivity of the reaction for upgradeable oxidized products, in particular that can be converted to cyclohexanol and cyclohexanone.

Furthermore, this selectivity is better and can only be maintained at an acceptable value if the concentration of oxidized products in the reaction medium is kept at a low value.

Consequently, the oxidation reaction is carried out by using a reaction medium that has a high concentration of hydrocarbon, this hydrocarbon acting as solvent. For the economy of the process, it is necessary to recover this non-oxidized hydrocarbon at the end of the reaction, in order to recycle it into the oxidation step and therefore to constitute a hydrocarbon circulation loop.

Moreover, the process for the oxidation of the hydrocarbon to peroxide and/or alcohol or ketone comprises steps of reacting and of separating the products contained in the reaction medium with removal of the fractions known as "light products", that is to say the products that have a boiling point below that of the hydrocarbon.

These various fractions of low boiling point products are often referred to in such processes as off-gases and are intended to be destroyed by incineration or burnt in a flare.

However, although the efficiency of the separation steps is high, the off-gases recovered still contain a small amount of non-oxidized hydrocarbon which it is highly advantageous to recover both from an environmental protection view point and from the view point of the economy of the process.

There is therefore a need for a process that makes it possible to economically and selectively recover the saturated hydrocarbon present in these off-gases in order to be able to recycle it into the oxidation process.

One of the objectives of the present invention is, in particular, to propose a process that makes it possible to treat the off-gases of a process for the oxidation of saturated hydrocarbons such as the oxidation of cyclohexane to cyclohexanol/cyclohexanone in order to recover the saturated hydrocarbon present in these off-gases and recycle it into the oxidation process.

For this purpose, the invention proposes a process for the oxidation of a saturated hydrocarbon via molecular oxygen comprising a process for treating gaseous effluents produced by said oxidation process, said treatment process comprises a step of bringing the gaseous effluents to be treated into contact with an oil in the liquid state in order to absorb the saturated hydrocarbon contained in the effluents and a second step of treating the hydrocarbon-loaded oil by water steam stripping (steam distillation) in order to extract the hydrocarbon, condensing the vapour recovered and separating the hydrocarbon by settling.

The process of the invention is a process for the oxidation of a saturated hydrocarbon comprising a process for treating the off-gases produced by the oxidation process and the steps of separating the various products, consisting in recovering the hydrocarbon present in these off-gases by absorption into a paraffinic and/or naphthenic oil, then in treating this oil containing the hydrocarbon via water steam stripping (steam distillation) in order to extract and recover the absorbed hydrocarbon and after separation, for example by condensation and settling, to recycle said hydrocarbon into the oxidation step.

According to one feature of the invention, the hydrocarbon is preferably a saturated hydrocarbon, advantageously a saturated cycloaliphatic hydrocarbon selected from the group consisting of cyclohexane, cyclooctane, cyclododecane and decalin.

The oxidation process may be a process for the oxidation of a hydrocarbon to an alkyl hydroperoxide, in the presence or absence of catalyst, then conversion of this alkyl hydroperoxide to ketone and/or alcohol. The oxidation process of the invention may also be a process for the oxidation, in the presence of a catalyst, via oxygen, of the hydrocarbon to alcohol and ketone in a single step. The process of the invention also applies to the treatments of the off-gases recovered in a process for the oxidation, via molecular oxygen, of a saturated hydrocarbon to diacid, such as the direct oxidation of cyclohexane to adipic acid.

In these processes, the oxidation is carried out with a large amount of hydrocarbon which acts as reactant and as solvent in order to prevent the concentration of oxidized products from being very high in the reaction medium.

These processes comprise several steps of reacting and of separating the products, especially of distilling the excess cyclohexane in order to recycle it to the oxidation step.

During these steps, it is common to recover a gaseous fraction comprising, in particular, the products having a low boiling point compared to the boiling point of the saturated hydrocarbon which cannot be upgraded. These gaseous fractions form most of the gaseous effluents of these oxidation processes and are often denoted by the expression off-gases. These off-gases are generally burnt, for example via a flare.

According to the process of the invention, the gaseous effluents or off-gases are treated in order to extract and recover the small amount of saturated hydrocarbon present and thus to be able to recycle it into the process. Furthermore, this recovery of the hydrocarbon reduces the amounts of waste and therefore is favourable to the protection of the environment.

According to the invention, this treatment consists in passing the off-gases or effluents into an oil in the liquid state, for example in a gas/liquid exchange or scrubber column.

When the oil is saturated with hydrocarbon or reaches a defined concentration level, the absorbed hydrocarbon is recovered via extraction with water steam. Thus, the oil is stripped (distilled) by steam, the hydrocarbon/steam mixture is condensed. The hydrocarbon is recovered by settling.

The oil suitable for the process of the invention should be chosen for some of these properties listed below:

- having a boiling point higher than that of the saturated hydrocarbon,
- being difficult to oxidize via oxygen in order to prevent and limit oil degradation phenomena,
- being a solvent for the saturated hydrocarbon,
- having a low vapour pressure at the steam stripping temperature,
- having a demixing property, via settling in the presence of water, which is sufficient to allow a water/oil separation compatible with an industrial exploitation.

Among the various oils available, paraffinic oils, naphthenic oils and mixtures thereof are particularly suitable for carrying out the process of the invention.

The process of the invention thus makes it possible to recover a considerable amount of hydrocarbon which may be evaluated from a few tenths of a percent to a few percent of the hydrocarbon involved in the oxidation process.

The scrubbing of the gaseous effluents by the oil and the steam stripping of the oil may be carried out in any suitable device known to a person skilled in the art such as gas/liquid exchange columns, plate or packed distillation columns, for example.

Other details and advantages of the invention will appear more clearly in the examples given below by way of indication.

EXAMPLE 1

In a process for the oxidation of cyclohexane to cyclohexanol and cyclohexanone, the gases to be released or off-gases originating from the reactors and from the various separation columns are brought together. The concentration of cyclohexane in these gases is between 8 and 12% by volume.

These gases are treated with a paraffinic oil such as the oil sold by BP France under the trade name Enerthene® 2367, fed at a temperature of 25° C. into a scrubber column comprising bubble trays. The gases exiting the scrubber column contain no more than 0.3% by volume of cyclohexane.

The oil loaded with cyclohexane is fed, after preheating to a temperature of 110° C., into the top part of a bubble tray distillation column operating at a pressure of 1.2 bar.

Water steam is fed into the bottom of the column. The azeotrope between the water and the cyclohexane is recovered at the top of the column and condensed. The condensates are introduced into a settling tank. The organic phase recovered is composed of cyclohexane and of light impurities. This organic phase is distilled in order to remove the light impurities. The cyclohexane recovered is recycled into the oxidation process.

EXAMPLE 2

In a process for the oxidation of cyclohexane to cyclohexanol and cyclohexanone, the gases to be released or off-gases originating from the reactors and from the various separation columns are brought together. The concentration of cyclohexane in these gases is between 5 and 7% by weight.

These gases are treated with a paraffinic and naphthenic oil such as the oil sold by SHELL under the trade name SHELL Edelex 912, fed at a temperature of 20° C. into a scrubber column comprising bubble trays. The gases exiting the scrubber column contain no more than 0.12% by weight of cyclohexane.

The oil loaded with cyclohexane is fed, after preheating to a temperature of 110° C., into the top part of a bubble tray distillation column operating at a pressure of 1.2 bar.

Water steam is fed into the bottom of the column. The azeotrope between the water and the cyclohexane is recovered at the top of the column and condensed. The condensates are introduced into a settling tank. The organic phase recovered is composed of cyclohexane and of light impurities. This organic phase is distilled in order to remove the light impurities. The cyclohexane recovered is recycled into the oxidation process.

EXAMPLE 3

In a process for the oxidation of cyclohexane to cyclohexanol and cyclohexanone, the gases to be released or off-gases originating from the reactors and from the various separation columns are brought together. The concentration of cyclohexane in these gases is between 7 and 9% by weight.

These gases are treated with a paraffinic and naphthenic oil such as the oil sold by SHELL under the trade name SHELL Edelex 912, fed at a temperature of 22° C. into a scrubber column comprising bubble trays. The gases exiting the scrubber column contain no more than 0.22% by weight of cyclohexane.

The oil loaded with cyclohexane is fed, after preheating to a temperature of 110° C., into the top part of a bubble tray distillation column operating at a pressure of 1.2 bar.

Water steam is fed into the bottom of the column. The azeotrope between the water and the cyclohexane is recovered at the top of the column and condensed. The condensates are introduced into a settling tank. The organic phase recovered is composed of cyclohexane and of light impurities. This organic phase is distilled in order to remove the light impurities. The cyclohexane recovered is recycled into the oxidation process.

The invention claimed is:

1. A process for oxidation of a saturated cycloaliphatic hydrocarbon via molecular oxygen, the process comprising:
   - oxidizing a saturated cycloaliphatic hydrocarbon via molecular oxygen, wherein gaseous effluents comprising saturated cycloaliphatic hydrocarbon are produced;
   - contacting the gaseous effluents with an oil in the liquid state in order to absorb the saturated cycloaliphatic hydrocarbon from such effluents, wherein the absorption produces a hydrocarbon loaded oil;
   - extracting hydrocarbon from the hydrocarbon loaded oil by treating the resulting hydrocarbon loaded oil by water steam stripping;
   - condensing the vapor recovered from the steam stripping; and
   - separating the hydrocarbon by settling, wherein the gaseous effluents are contacted with the oil at a temperature of from 20° C. to 25° C.

2. The process as defined by claim 1, wherein the hydrocarbon is selected from the group consisting of cyclohexane, a cyclooctane, a cyclododecane, and a decalin.

3. The process as defined by claim 1, wherein the oil is selected from the group consisting of a paraffinic oil, a naphthenic oil, and a mixture thereof.

4. The process as defined by claim 1, wherein the process is used for oxidation of a saturated hydrocarbon to hydro-peroxide, alcohol and/or ketone.

5. The process as defined by claim 1, wherein the process is used for oxidation, via oxygen, of cyclohexane to adipic acid.

* * * * *